(12) United States Patent
MacDonald et al.

(10) Patent No.: US 7,976,855 B2
(45) Date of Patent: *Jul. 12, 2011

(54) METAL ION MODIFIED HIGH SURFACE AREA MATERIALS FOR ODOR REMOVAL AND CONTROL

(75) Inventors: John Gavin MacDonald, Decatur, GA (US); Bao Trong Do, Decatur, GA (US); Kelly D. Arehart, Roswell, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 11/227,506

(22) Filed: Sep. 15, 2005

(65) Prior Publication Data

US 2006/0008442 A1    Jan. 12, 2006

Related U.S. Application Data

(63) Continuation-in-part of application No. 10/137,052, filed on Apr. 30, 2002.

(51) Int. Cl.
  *A61K 51/02* (2006.01)
  *A61K 47/02* (2006.01)
  *A61K 8/02* (2006.01)
  *A61K 8/19* (2006.01)
(52) U.S. Cl. .......... 424/402; 424/400; 424/401
(58) Field of Classification Search .......... None
  See application file for complete search history.

(56) References Cited

U.S. PATENT DOCUMENTS

| | | | |
|---|---|---|---|
| 3,013,897 A | 12/1961 | Cupery et al. | |
| 4,172,781 A | 10/1979 | Walk et al. | |
| 4,313,820 A | 2/1982 | Farha, Jr. et al. | |
| 4,525,410 A * | 6/1985 | Hagiwara et al. | 428/198 |
| 4,725,415 A | 2/1988 | Kidd | |
| 4,775,585 A | 10/1988 | Hagiwara et al. | |
| RE32,957 E * | 6/1989 | Elias et al. | 604/368 |
| 4,836,141 A | 6/1989 | Whitfield | |

(Continued)

FOREIGN PATENT DOCUMENTS

CA    2350757 A1    5/2000

(Continued)

OTHER PUBLICATIONS

Malik et al.: *Characterisation of Novel Modified Active Carbons and Marine Alga Biomass for the Selective Adsorption of Lead*, Water Research 36, pp. 1527-1538, 2002.

(Continued)

*Primary Examiner* — Anand Desai
*Assistant Examiner* — Melissa S Mercier
(74) *Attorney, Agent, or Firm* — Dority & Manning, P.A.

(57) ABSTRACT

This invention relates to modified high surface area materials, such as nanoparticles that are coated with metal ions, and articles treated with the modified high surface area materials. The modified nanoparticles have active sites that bind various gases and/or odorous compounds, thereby removing these compounds from a medium such as air or water. Metal ions are adsorbed onto the surface of the nanoparticle and bound strongly to the surface. By selection of the metal ion, specific gaseous compounds and/or odorous compounds can be targeted and removed efficiently and effectively from both aqueous phase and from the air. The modified nanoparticles are applied to nonwoven webs to provide odor removing articles for industrial and consumer use in refrigerators and trash containers.

23 Claims, 5 Drawing Sheets

U.S. PATENT DOCUMENTS

| | | | |
|---|---|---|---|
| 4,988,505 | A | 1/1991 | Watanabe et al. |
| 5,064,599 | A | 11/1991 | Ando et al. |
| 5,102,592 | A | 4/1992 | McCauley et al. |
| 5,108,739 | A | 4/1992 | Kurihara et al. |
| 5,120,693 | A | 6/1992 | Connolly et al. |
| 5,122,418 | A | 6/1992 | Nakane et al. |
| 5,180,585 | A * | 1/1993 | Jacobson et al. .............. 424/405 |
| 5,183,656 | A | 2/1993 | Uesaka et al. |
| 5,407,442 | A | 4/1995 | Karapasha |
| 5,429,628 | A | 7/1995 | Trinh et al. |
| 5,480,636 | A * | 1/1996 | Maruo et al. ............... 424/76.21 |
| 5,486,356 | A * | 1/1996 | Yim ............................. 424/76.1 |
| 5,534,249 | A | 7/1996 | Maurer |
| 5,580,655 | A | 12/1996 | El-Shall et al. |
| 5,595,750 | A | 1/1997 | Jacobson et al. |
| 5,663,224 | A | 9/1997 | Emmons et al. |
| 5,843,267 | A * | 12/1998 | Cashaw et al. ................ 156/324 |
| 5,861,144 | A | 1/1999 | Peterson et al. |
| 5,874,067 | A | 2/1999 | Lucas et al. |
| 5,882,638 | A | 3/1999 | Dodd et al. |
| 5,885,262 | A | 3/1999 | Wheeler |
| 5,885,599 | A | 3/1999 | Peterson et al. |
| 5,948,398 | A | 9/1999 | Hanamoto et al. |
| 6,096,299 | A | 8/2000 | Guarracino et al. |
| 6,254,894 | B1 | 7/2001 | Denkewicz, Jr. et al. |
| 6,299,867 | B1 | 10/2001 | Aoyagi et al. |
| 6,344,218 | B1 | 2/2002 | Dodd et al. |
| 6,410,616 | B1 * | 6/2002 | Harada et al. ................. 523/337 |
| 6,447,373 | B1 | 9/2002 | Lack et al. |
| 6,858,147 | B2 | 2/2005 | Dukhin et al. |
| 2001/0023338 | A1 * | 9/2001 | Guarracino et al. .......... 604/360 |
| 2001/0031248 | A1 | 10/2001 | Hall-Puzio et al. |
| 2002/0005145 | A1 | 1/2002 | Sherman |
| 2002/0096518 | A1 | 7/2002 | Foster, Sr. |
| 2002/0132070 | A1 | 9/2002 | Franzen et al. |
| 2002/0141898 | A1 | 10/2002 | Carlucci et al. |
| 2002/0149656 | A1 * | 10/2002 | Nohr et al. ....................... 347/95 |
| 2002/0151634 | A1 * | 10/2002 | Rohrbaugh et al. .......... 524/430 |
| 2002/0182102 | A1 | 12/2002 | Fontenot et al. |
| 2003/0078552 | A1 | 4/2003 | Tepper et al. |
| 2003/0087086 | A1 | 5/2003 | Koslow et al. |
| 2003/0226773 | A1 | 12/2003 | Shaffer |
| 2005/0084412 | A1 | 4/2005 | MacDonald et al. |
| 2005/0084438 | A1 | 4/2005 | Do et al. |
| 2005/0084464 | A1 | 4/2005 | McGrath et al. |
| 2005/0084632 | A1 | 4/2005 | Urlaub et al. |
| 2005/0085144 | A1 | 4/2005 | MacDonald et al. |
| 2005/0112085 | A1 | 5/2005 | MacDonald et al. |
| 2005/0181067 | A1 | 8/2005 | Yokoyama et al. |

FOREIGN PATENT DOCUMENTS

| | | |
|---|---|---|
| CN | 1287878 | 3/2001 |
| DE | 101 16 192 | 9/1957 |
| EP | 0 251 783 | 1/1988 |
| EP | 0 572 914 | 12/1993 |
| EP | 1 053 788 | 1/2000 |
| EP | 1053788 | * 11/2000 |
| WO | WO 00/29311 | 5/2000 |
| WO | WO 01/89411 | 11/2001 |
| WO | WO 02/26272 | 4/2002 |
| WO | WO 02/98747 | 12/2002 |
| WO | WO 02/98765 | 12/2002 |
| WO | WO 03/092885 | 11/2003 |
| WO | WO 2004/079075 | 9/2004 |
| WO | WO 2006/111402 | 10/2006 |

OTHER PUBLICATIONS

Abstract of Article—*Dimerization of tert-butylmercaptain over the surface of aerosol impregnated with copper and manganese*, Korean Chemical Society, Aug. 16, 2000, 1 page.

* cited by examiner

METAL ION MODIFIED HIGH SURFACE AREA MATERIALS FOR ODOR REMOVAL AND CONTROL

This application is a continuation-in-part of U.S. application, Ser. No. 10/137,052, filed on 30 Apr. 2002. The co-pending parent application is hereby incorporated by reference herein in its entirety and is made a part hereof, including but not limited to those portions which specifically appear hereinafter.

FIELD OF THE INVENTION

This invention relates to modified high surface area materials useful in neutralizing or removing gases and/or odorous compounds. The high surface area material, such as a nanoparticle, is coated with metal ions that can bind with gas molecules and/or odorous compounds. The modified high surface area materials can be incorporated into various industrial and consumer products including absorbent articles, air and water filters, household cleaners, fabrics, and paper towels.

BACKGROUND OF THE INVENTION

Many attempts have been made to formulate an effective odor removal system and various consumer products are available for combating odorous compounds. Some products are designed to cover up odors by emitting stronger, more dominant odors, examples including scented air freshener sprays and candles. Another way to combat odorous compounds, including ammonia, methyl mercaptan, trimethylamine, and other various sulfides and amines, is to remove these compounds from a medium by deodorizing agents that will absorb these compounds.

Activated charcoal and sodium bicarbonate are two compounds commonly used to absorb odors. However, activated charcoal typically has a low deodorizing ability, especially for ammonia odors and when in the presence of moisture, and the black color of charcoal lacks aesthetically pleasing characteristics desired in absorbent articles such as diapers. Sodium bicarbonate, and other white odor absorbents such as silica gel and zeolites, generally have a lower absorbency than activated charcoal and are therefore less effective.

Titanium oxide particle, such as taught in U.S. Pat. No. 5,480,636 issued to Maruo et al., are also useful in removing a few odors such as ammonia. U.S. Pat. No. 5,480,636 teaches adding zinc oxy or silicon oxy compounds to the titanium oxide to broaden the titanium oxide deodorizing capabilities. However, this approach is still limited by the photocatalytic nature of the titanium dioxide which requires light in order to convert odorous compounds into non-odorous compounds. Also the titanium oxide compounds as disclosed in U.S. Pat. No. 5,480,636 are not useable in aqueous solutions.

In addition to foul smelling compounds, there is a need for products capable of removing gases that, while not necessarily odorous, still cause a negative effect. One example of such a gaseous compound is ethylene. Ethylene, a natural hormone, is released by fruits as a ripening agent. By removing ethylene gas, fruit ripening could be slowed and controlled, allowing for extended storage and transportation.

There is a need for a gas and/or odor removal/neutralizing compound that is effective both dry and in solution. There is a need for an effective odor removal/neutralizing compound that can be used in various industrial and consumer products. There is a need for a gas and/or odor removal/neutralizing compound that can be easily applied to various surfaces and materials.

SUMMARY OF THE INVENTION

This invention relates to high surface area materials that are coated with metal ions. These modified high surface area materials have active sites that bind at least one gaseous compound and/or odorous compound, thereby removing these compounds from a medium such as air or water. Nanoparticles are a type of high surface area materials useful in this invention to remove at least one of gaseous compounds and odorous compounds. At least one type of metal ion is adsorbed onto the surface of the nanoparticle and bound strongly to the surface. By selection of the metal ion, certain gaseous compounds and/or odorous compounds can be targeted and removed efficiently and effectively from both aqueous phase and from the air. This invention uses high surface area nanoparticles as templates to adsorb specific functionalities (metal ions) that target at least one of gaseous compounds and odorous compounds and form complexes with them and remove them from the media. For example, silica nanoparticles modified by copper ions (or alternatively, silver ions) were demonstrated to be effective in removing amine and sulfur based classes of odorous compounds.

It is one object of this invention to create an effective gaseous compound removal system. The invention is useful in various industrial and consumer products. It is another object of this invention to create a gaseous compound removal system for inhibiting the ripening of plant materials.

It is another object of this invention to create an effective odor removal compound useful in both aqueous phase and in the air. It is another object of this invention to create an effective odor removal compound that can effectively be used in various industrial and consumer products. This invention can be used in combination with various products for the removal of odors.

The general object of this invention can be attained, at least in part, through an odor absorbing article of manufacture. The article includes a substrate treated with a high surface area material. The high surface material includes at least one metal ion adsorbed onto the high surface area material.

The invention further provides an odor absorbing article of manufacture including a nonwoven web and a plurality of modified nanoparticles disposed on the nonwoven web. Each of the plurality of modified nanoparticles includes a plurality of metal ions adsorbed onto a nanoparticle. At least one of the nanoparticle and the metal ion is capable of binding at least one compound selected from the group of a gaseous compound, an odorous compound, and combinations thereof.

The invention still further provides an odor absorbing article of manufacture including a nonwoven web and a plurality of modified silica nanoparticles disposed on the nonwoven web. Each of the plurality of modified silica nanoparticles includes a plurality of transition metal ions adsorbed onto a silica nanoparticle. The plurality of transition metal ions comprises ions selected from the group consisting of copper ions, silver ions, gold ions, iron ions, manganese ions, cobalt ions, nickel ions, and combinations thereof.

Modified high surface area materials of this invention are also useful in absorbent articles such as diapers and feminine products for removing odors. Modified high surface area materials of this invention are useful in filtration devices and coated onto walls, wall paper, and glass for removal of odors. Modified high surface area materials of this invention are useful in oral care products such as mouthwash and chewing gum for the removal of compounds in the mouth that cause unpleasant odors.

The foregoing and other features and advantages will become further apparent from the following detailed description of the presently preferred embodiments read in conjunction with the drawings.

DETAILED DESCRIPTION OF THE PRESENTLY PREFERRED EMBODIMENTS

This invention relates to high surface area materials, such as nanoparticles, modified with at least one metal ion. The modified high surface area materials of this invention are useful in removing gaseous compounds and/or odorous compounds. "Gaseous compound" or "gas" includes any molecule or compound that can exist as a gas or vapor. "Odorous compound" or "odor" refers to any molecule or compound detectable to the olfactory system. Odorous compounds can exist as a gaseous compound and can also be present in other media such as liquid.

The high surface area materials of this invention have at least one metal ion present on the surface of the high surface area material, and the metal ion creates an active site that binds with at least one gaseous compound and/or odorous compound thereby removing the compound from the surrounding environment. High surface area materials can also absorb certain gaseous compounds and/or odorous compounds from the surrounding environment by adsorption directly onto the surface area of the high surface area materials.

Gas and/or odor removing particles of this invention are modified high surface area materials. High surface area materials useful in this invention have a large surface area due to the small size of the individual particles of the high surface area material. High surface area materials useful in this invention have a suitable surface area of at least about 200 square meters/gram, more suitably about 500 square meters/gram, and more suitably about 800 square meters/gram.

Figure 1:
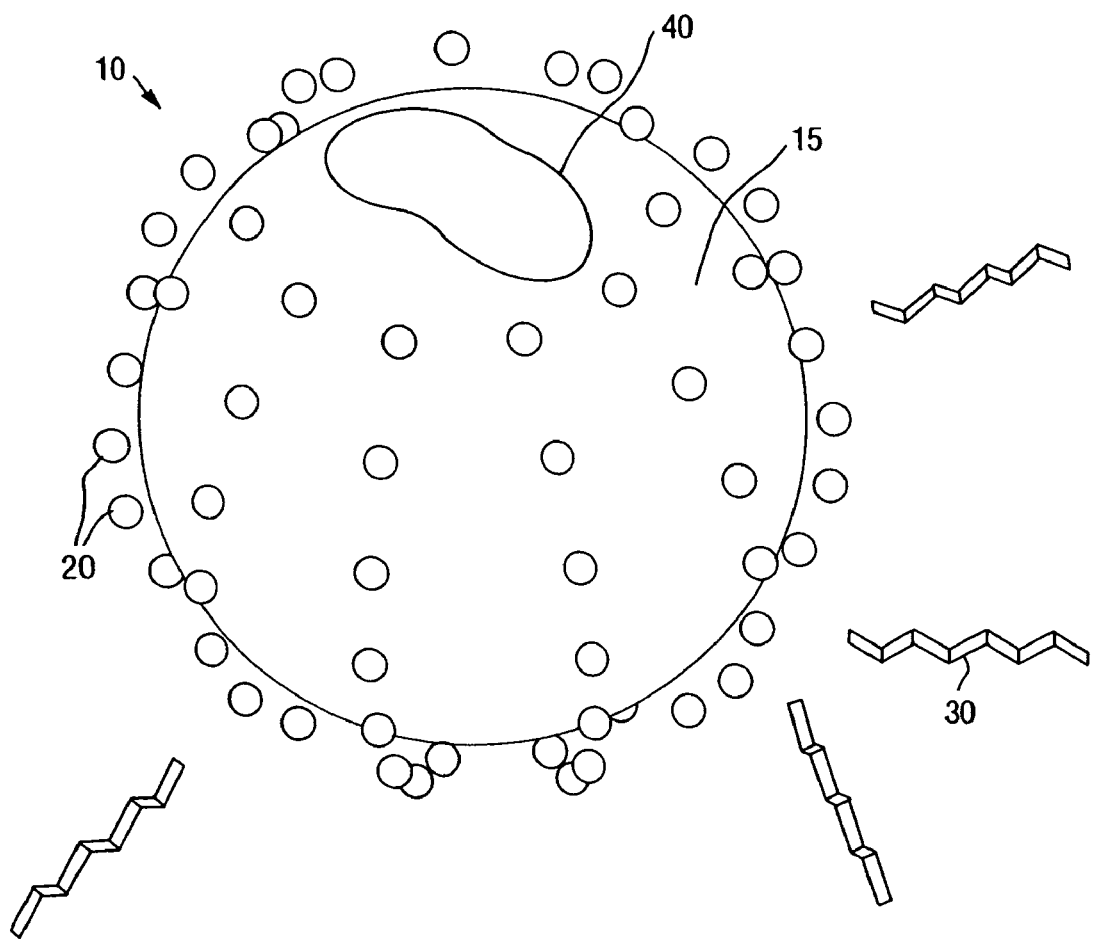
FIG. 1 is a drawing of a modified nanoparticle according to one embodiment of this invention.

Nanoparticles are examples of high surface area materials useful in this invention. "Nanoparticle" refers to a high surface material having a particle diameter of less than about 500 nanometers. While the invention will be described hereinafter with particular reference to nanoparticles, it will be understood that the invention is useful with various high surface area materials. FIG. 1 shows a modified nanoparticle 10 according to one embodiment of this invention, useful as a gas and/or odor removing particle. The modified nanoparticle 10 includes a nanoparticle 15 and metal ions 20. FIG. 1 shows a plurality of metal ions 20; however modified nanoparticle 10 can have various amounts of metal ions 20 and will have at least one metal ion 20. The modified nanoparticle 10 is useful for removing various gaseous compounds and/or odorous compounds. The specific compound to be removed is generally dependent on the specific metal ions 20 used and the type of nanoparticle 15.

Nanoparticles useful in this invention include, without limitation, silica, alumina, magnesium oxide, titanium dioxide, iron oxide, gold, zinc oxide, copper oxide, organic nanoparticles such as polystyrene, and combinations thereof. Nanoparticles are not generally ionic yet still have an overall electric Zeta Potential. "Zeta Potential" refers to the electrical potential, or electrokinetic potential, that exists across the interface of all solids and liquids. Nanoparticles with either positive or negative Zeta Potentials are known. Natural occurring chemical reactions on the surface of a nanoparticle result in the Zeta Potential of that nanoparticle. For example, silica nanoparticles are tetrahedral complexes of silicon dioxide molecules. On the surface of the silica particles the silicon dioxide molecules can undergo chemical reactions forming silanol groups (SiOH) the silanol groups reacting with other silanol groups to form siloxane bonds (Si—O—Si bonds). The dehydration reactions of the silanol groups to form the silanol bond and the reverse reactions result in a negative Zeta Potential and allow positively charged metal ions to adsorb onto the silica.

The nanoparticles useful in this invention will typically have a first Zeta Potential and a second Zeta Potential after adsorption of the metal ion onto the nanoparticle due to the addition of the oppositely-charged metal ions. The Zeta Potential change of the nanoparticle is related to the amount of metal ions adsorbed onto the nanoparticle. This relationship provides a measurement for determining the amount of adsorbed metal ions and a method for controlling the amount of adsorption. For instance, the addition of a dilute solution of copper chloride drop-wise to a silica nanoparticle solution until the Zeta Potential of the silica suspension changed from $-25$ millivolts to a higher Zeta Potential, such as in the range of about $-5$ millivolts to $-15$ millivolts, was found to be provide a sufficient concentration of metal ions adsorbed onto the nanoparticles to remove particular odorous compounds. In one embodiment of this invention the nanoparticle has a difference between the first and second Zeta Potential of at least about 1.0 millivolt and suitably at least about 5.0 millivolts.

The nanoparticles of this invention are modified with metal ions that ionically bond with compounds such as gases and odorous compounds. "Metal ion" refers to salt ions and/or ion complexes of transition metal elements designated as IB through VIIIB on the periodic table. Other ions can be used in the invention as well. Metal ions are adsorbed onto high surface area materials due to differences in electric potential. Positively charged metal ions are adsorbed onto a negatively charged surface of a nanoparticle and vice versa. Examples of metal ions useful in this invention include, without limitation, copper ion ($Cu^{+2}$), silver ion ($Ag^{+1}$), gold ion ($Au^{+1}$ and $Au^{+3}$), iron (II) ion ($Fe^{+2}$), iron (III) ion ($Fe^{+3}$), permanganate ion ($MnO_4^{-1}$), and combinations thereof. In one embodiment of this invention, the modified nanoparticles include about 20-200 metal ions per nanoparticle, and typically and more desirably about 40-75 metal ions per nanoparticles.

In one embodiment of this invention the nanoparticle useful in this invention has a negative Zeta Potential and adsorbs positively charged metal ions. One suitable nanoparticle has a negative Zeta Potential of about $-1$ to $-50$ millivolts and suitably about −1 to −20 millivolts. In one embodiment of this invention the nanoparticle having a negative Zeta Potential is a silica nanoparticle. Silica nanoparticles useful in this invention are available from Nissan Chemical Industries, Ltd., Houston, Tex., under the name SNOWTEX®, have a particle size range of 1-100 nanometers. The silica nanoparticle can be modified with a positively charged metal ion such as copper ions, silver ions, gold ions, iron ions, and combinations thereof.

In another embodiment of this invention the nanoparticle useful in this invention has a positive Zeta Potential and adsorbs negatively charged metal ion complexes. One suitable nanoparticle has a positive first Zeta Potential of about 1 to 70 millivolts and suitably about 10 to 40 millivolts. In one embodiment of this invention the nanoparticle having a positive Zeta Potential is an alumina nanoparticle. Alumina nanoparticles are also available from Nissan Chemical Industries, Ltd., Houston, Tex., under the name ALUMINASOL®, and have size ranges of about 1-300 nanometers. The alumina nanoparticle can adsorb negatively charged metal ions and metal ion complexes such as permanganate ions.

Current odor control materials such as activated charcoal or sodium bicarbonate rely on the surface area to absorb certain odors. Using these materials is not as effective at odor removal as the modified high surface area materials of this invention. The addition of a metal ion adsorbed onto the surface of a nanoparticle, as in this invention, provides an active site for capturing and neutralizing gases and odorous compounds, such as sulfur, nitrogen, and/or oxygen containing compounds. In addition, the modified nanoparticles of this invention still have the large surface area that is useful in absorbing other odorous compounds. The metal ion active sites of the modified nanoparticles are particularly useful in removing odorous compound such as mercaptans, ammonia, amines, and mono- and disulfides. Other odorous compounds such as aliphatic ketones, carboxylic acids, aliphatic aldehydes, and aliphatic terpenoids can be removed by adsorption onto the large surface area of the modified nanoparticles. Modified nanoparticles are useful in removing odors caused by sulfides, disulfides, trisulfides, thiols, mercaptans, ammonia, amines, isovaleric acid, acetic acid, propionic acid, hexanal, heptanal, 2-butanone, 2-pentanone, 4-heptanone, and combinations thereof. Modified nanoparticles can also remove gases such as ethylene gas, carvone, dienals, and terpenoids.

More than one type of metal ion can be coated on a nanoparticle. This has an advantage in that certain metal ions may be better at removing specific gases and/or odorous compounds than other metal ions. In one embodiment of this invention more than one type of metal ion are adsorbed onto a nanoparticle for more effectively removing more than one type of gaseous compound or odorous compound from a medium. In one embodiment of this invention more than one type of metal ion are adsorbed onto a nanoparticle for removing at least one gaseous compound and at least one odorous compound from a medium.

Modified nanoparticles of this invention can be used in combination with other modified nanoparticles for effective removal of various gases and odors. In one embodiment of this invention copper ion modified silica nanoparticles are used in combination with permanganate ion modified magnesium oxide nanoparticles. By using the two different modified nanoparticles in combination, numerous odorous compounds can be removed. For example, the modified silica nanoparticle is useful for removing sulfur and amine odors and the modified magnesium oxide nanoparticle is useful in removing carboxylic acid odors. Combining modified nanoparticles of this invention allow for removal of a broader range of odors.

Modified nanoparticles are made by mixing nanoparticles with solutions containing metal ions. Such solutions are generally made by dissolving metallic compounds into a solvent resulting in free metal ions in the solution. The metal ions are drawn to and adsorbed onto the nanoparticles due to the electric potential differences. The Zeta Potential of a nanoparticle changes after the adsorption of metal ions according to this invention. Thus the Zeta Potential can be used to monitor the adsorption of metal ions onto the nanoparticle.

Modified high surface area materials according to this invention are versatile and can be used alone or in combination with other articles of manufacture for effective odor removal and control. Unlike activated charcoal deodorants, the modified nanoparticles of this invention maintain their odor neutralizing effects in solution. The modified nanoparticles of this invention also maintain odor neutralizing properties when dry and in aerosol form. This versatility allows for uses in various commercial products. Other advantages of the modified nanoparticles are that they are colorless in solution and white in powder form (activated charcoal is typically black). Modified high surface area materials of this invention can also be used in combination with other commercially available odor removal materials.

Modified nanoparticles of this invention can be applied to various substrate materials. In one embodiment of this invention modified nanoparticles are held onto a surface of a material by the electrical potential differences between the modified nanoparticle (Zeta Potential) and the material surface (Streaming Potential). Modified nanoparticles of this invention can be applied as a solution to a material surface and dried, resulting in a surface that absorbs gas and/or odors.

In one embodiment of this invention a substrate is treated with a modified high surface area material to provide or produce an odor absorbing article of manufacture. The modified high surface area material, such as a nanoparticle, includes at least one metal ion adsorbed onto the high surface area material. In one embodiment, the substrate is desirably a gas permeable material, such as, for example, a nonwoven web made from various and alternative polymers and/or natural fibers, a woven fabric, or a breathable film. Various and alternative nonwoven webs or fabrics are available for use as the substrate in this invention, such as, for example, airlaid webs, meltblown webs, spunbond webs, bonded carded webs, and/or coform webs, including those made from thermoplastic materials, such as polyolefins (e.g., polyethylene and polypropylene homopolymers and copolymers), polyesters, polyamines, and the like, or natural fibers such as wood pulp fibers, cotton fibers, or other cellulose fibers.

Figure 4:
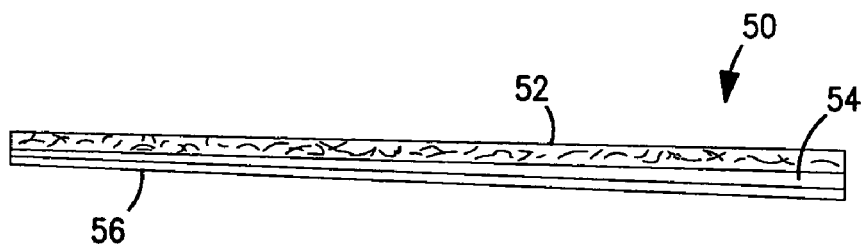
FIG. 4 is a side view of an odor absorbing article according to one embodiment of this invention.

FIG. 4 illustrates a side view of an odor absorbing article according to one particularly preferred embodiment of this invention. The article is a sticker 50 that can be attached to an object and used to absorb odors from the environment surrounding the sticker 50 and/or the object. The sticker 50 includes a substrate 52 that is treated with a modified high surface material of this invention, such as, for example, a plurality of silica nanoparticles having copper and/or iron ions adsorbed thereon. In one embodiment of this invention, the substrate 52 is a gas permeable material, such as a nonwoven web or a microporous film.

The sticker 50 includes an adhesive material 54 on one side of the substrate 52. The adhesive material 54 desirably allows for the attachment of the sticker 50 to a surface when and where the odor absorbing properties of the sticker 50 are desired. The odor absorbing sticker 50 can, desirably, be easily placed and removed on the intended surface. Various and alternative adhesive materials are available for use as the adhesive material 54, and desirably the adhesive material 54 is a removably attachable adhesive, as is known and available to those skilled in the art. The adhesive material 54 can be directly or indirectly applied to the substrate 52. For example, the adhesive material can be a double-sided tape, such as a double-sided foam tape, or can be an adhesive extruded onto the substrate 52, as is also known to those skilled in the art. In another embodiment, the adhesive material can be applied indirectly to the substrate by a hook and loop style fastener. An optional removable layer 56, such as is also known and available to those skilled in the art, can be disposed over the adhesive material 54 to protect and maintain the adhesive properties of the adhesive material 54 until use of the sticker 50.

In one embodiment of this invention the sticker 50 is appropriately sized to be applied to a surface within a refrigerator. The removable layer 56 is removed and the sticker 50 is adhered to, for example, an interior side wall of the refrigerator. As will be appreciated by those skilled in the art following the teachings herein provided, the sticker 50 is desirably placed where the air circulation is high, which is typically along the interior walls of a refrigerator.

Odors generated in refrigerators typically result from oxidation or enzymatic conversions of particular chemicals in aging vegetable, fruits, and meats. Examples of such reactions include, without limitation, deamination of amino acids to generate ammonia, decomposition of sulfur containing amino acids to generate mercaptans and sulfides, and decomposition of sugars and amino acids to generate odorous aliphatic acids. As will be demonstrated below in the Examples, the odor adsorbing sticker of this invention adhered to the interior refrigerator wall is effective to reduce or eliminate these and other odors and gases within the refrigerator.

In one embodiment of this invention, the substrate 52 includes a nonwoven web. Desirably, the nonwoven web is impregnated with the modified high surface material, such that the modified high surface material is disposed on fiber surfaces of the individual fibers in the nonwoven web. As will be appreciated by those skilled in the art following the teachings herein provided, the plurality of individual fibers within the nonwoven web desirably provides an increase in the surface area which can be treated with the modified high surface area materials. When a portion of circulating air passes throughout the pores between, and over the treated surface of, the individual treated fibers of the nonwoven web, the modified high surface material removes gaseous compounds and/or odorous compounds from the portion of the circulated air. In addition, the circulating air may cause the removal of an amount of the modified high surface area materials from the fiber surfaces, thereby circulating the odor removing particles through the air stream, such as, for example, throughout a refrigerator. The sticker 50 has the additional desirable benefit of being discrete, by laying flat against the interior refrigerator wall.

The sticker of one embodiment of this invention is placed over an air flow passageway, thereby causing the air flow to pass through the nonwoven web. For example, referring to a refrigerator, a treated nonwoven web sticker of this invention can be placed over an air duct, for example, an air intake and/or outlet, such that the circulating air passes through the treated nonwoven web. Desirably in such an embodiment of this invention, the adhesive material is disposed on only a portion of one side of the treated nonwoven web, such as around, along, or about an outer peripheral edge, thereby reducing or eliminating interference with or restriction of the air flow through the sticker substrate. As will be appreciated by those skilled in the art following the teachings herein provided, the size, shape, and configuration of the nonwoven web, and the amount and placement of the adhesive material, can vary depending on need and the size and shape of the opening the sticker is to be disposed over.

In another embodiment, the odor absorbing article of manufacture of this invention is a container formed, at least in part by a substrate, desirably a rigid substrate such as cardboard or other cellulosic or pulp material, treated with the modified high surface area material. In one particularly preferred embodiment, the container includes an outermost layer treated to create an odor absorbing three-dimensional functional container that can be used to eliminate odors in a variety of environments, including, but not limited to the refrigerator environment. As an example of such a container, a box containing baking soda was coated with the modified high surface area material of this invention, placed in a refrigerator and was demonstrated to remove odors more effectively than an untreated box tested under similar odor generating conditions. As will be appreciated by those skilled in the art following the teachings herein provided, various and alternative shapes, sizes, materials, and configurations are available for the container of this invention. Also, any of the modified high surface area materials of this invention can be used, alone or in various combinations.

In another embodiment of this invention a substrate is treated with a modified high surface area material to provide or produce an odor absorbing article for remediation of garbage odors. The substrate and modified high surface area material can be any substrate and modified high surface area material discussed herein. In one exemplary embodiment of this invention, the substrate is a gas permeable material such as a nonwoven web, and the modified high surface material is a plurality of copper ion and/or iron ion modified silica nanoparticles. The treated substrate is cut into a plurality of small, confetti-like material pieces that can be put or sprinkled into a trash container, such as a trash bag or trash can, or other container where removing odors is desired. The material pieces are "confetti-like" in that they are small bits or pieces of the treated gas permeable material that can be taken in hand by an end user and dropped, tossed, or otherwise placed in a trash or other container.

As will be appreciated by those skilled in the art, various and alternative sizes, shapes, colors, and configurations are available for the material pieces. In one embodiment of the invention, the substrate is cut, shredded, or ground into a plurality of material pieces having an average material piece outer surface area of about 2 $cm^2$ or less, more suitable about 1 $cm^2$ or less, desirably about 0.5 $cm^2$ or less, and more desirably about 0.25 $cm^2$ or less. As used herein, the "piece outer surface area" refers to the area of the external surface or outer periphery of the material piece, and not, for example, the total surface area provided by the individual fibers of a nonwoven web. The material pieces can include a flat or planar configuration, or have a three-dimensional configuration. The material pieces can be shaped, for example, as circles, spheres, squares, cubes, triangles, rectangles, and combinations thereof. The material pieces can also include irregular flat or three-dimensional configurations.

The odors generated in typical household trash are often from the same chemical reactions discussed above for refrigerator odors. Thus the treated substrate of this invention is also suitable for removing the odors common in trash. Providing the treated substrate in a plurality of material pieces allows the consumer to sprinkle the pieces into the garbage as needed, thereby allowing the consumer to control the timing and quantity of the application. In one preferred embodiment of this invention the confetti-like material pieces are a plurality of nonwoven web pieces treated with metal ion modified silica nanoparticles.

The modified nanoparticles of this invention are also useful in air filters, such as house filters, vent filters, disposable face masks, and face mask filters. In another embodiment, the modified nanoparticles can be applied to walls, wallpaper, glass, toilets, and/or countertops. For instance, the modified nanoparticles can be used in a restroom facility. Other uses include without limitation refrigerator mats and fabric softener sheets.

In one embodiment of this invention, the modified nanoparticles are coated onto a fibrous cloth. Various types of fibrous cloths are useful in this invention including, without limitation, cloth made from natural fibers such as wood pulp fibers, cotton fibers, and other plant fibers, and nonwoven webs including spunbond webs, meltblown webs, carded fiber webs, air laid webs, and the like, made from thermoplastic materials such as polyolefin (e.g. polyethylene and polypropylene homopolymers and copolymers), polyesters, polyamines, and the like. Modified nanoparticles can be coated on various types of fabric, film, or fibers. Modified nanoparticles can be coated in various amounts depending on need. Suitably, modified nanoparticles are coated on nonwoven webs, fabrics, films, or fibers in an amount of about 0.001 to 10.0 grams per square meter and more suitably about 0.1 grams per square meter.

The modified nanoparticles are also useful to absorb gases that plants produce to ripen fruit. Ethylene gas is produced by plants as a hormone to aid fruit ripening. By removing ethylene gas as it is produced, fruit ripening can be slowed and controlled. Permanganate ion modified alumina nanoparticles are useful in removing ethylene gas. In one embodiment, the permanganate ion modified alumina nanoparticles are adsorbed onto spunbond polypropylene fabric. The fabric has a negative streaming potential and the positively charged nanoparticles are held strongly onto the fiber surface. The fabric can then be used in packaging and storing fruit such as bananas to inhibit ripening by removing ethylene gas. The fabric can be used to wrap the fruit, as a bag to hold the fruit, or swatches can be included in the current packaging. The modified nanoparticles can also be sprayed onto a box or other packaging material used in transportation and storage of fruit. In one embodiment the cloth has a purple color due to the permanganate ions, and when the fabric is saturated with ethylene the fabric changes to a brown color. This color change acts as an indicator that the fabric needs replacement.

Modified nanoparticles of this invention are useful in removing odorous compounds from solutions such as water and urine. The modified nanoparticles could be applied to water treatment systems for use in removing sulfurous compounds from well water or in toilet tanks to reduce the odors resulting from urine. The modified nanoparticles of this invention are so effective against removing offensive components in urine that the yellow color often present in urine is neutralized, leaving a clear liquid. The modified nanoparticles of this invention could also be used in liquid detergents and household cleaners to remove odors.

In one embodiment of this invention, the modified nanoparticles are applied to an absorbent article. The term "absorbent article" includes without limitation diapers, training pants, swim wear, absorbent underpants, baby wipes, adult incontinence products, feminine hygiene products, absorbent tissues, medical garments, underpads, bandages, absorbent drapes, and medical wipes, as well as industrial work wear garments. In one embodiment the modified nanoparticles can be added to the absorbent material of these products. In another embodiment the modified nanoparticles can be applied as a coating on any fabric or film layer, such as the inner liner or outer cover of a diaper. In one embodiment the modified nanoparticles can be applied as a coating on a breathable film of an outer cover of an absorbent article such as a diaper or incontinence product to absorb odors. The modified nanoparticles can also be applied to paper towels and wet wipes for use in cleaning odorous liquids. The absorbent articles absorb the odorous liquid and the modified nanoparticles bind the odorous compounds from the liquid neutralizing the smell.

In another embodiment of this invention, the nanoparticles are used as aerosol odor neutralizers/deodorants. The modified nanoparticles are packaged with a propellant that allows spraying the modified nanoparticles into the air for removal of gases and odorous compounds. The modified nanoparticles can be used in a household air freshener or be used in combination with a mist emitted from a vaporizer or humidifier.

The modified nanoparticles can be used in oral care. Sulfur and amine compounds are often the reason for bad breath. Modified nanoparticles can be added to oral care products such as mouth washes, oral-care chewing gums, toothpaste, and/or toothbrush fibers. Using a silica nanoparticle modified with copper ions would be one such modified nanoparticle useful in oral care. Silica is widely used in toothpastes as an abrasive and the modified nanoparticles typically contain small levels of copper ions, far below levels in multiple vitamin tablets. Thus there should not be a health concerns with this use of the modified nanoparticles.

The modified nanoparticles are also useful as a breath indicator. Modified nanoparticles can be used as a color indicator in the presence of odorous compounds. In one embodiment of this invention a cellulose wipe coated with copper ion modified silica nanoparticles is placed in a plastic tube such as a straw. When the user breathes into the straw the cellulose wipe turns from green to blue indicating odors such as ammonia vapor or sulfur compounds. A color change can occur with even a low amount of odorous compounds.

Example 1

A dilute suspension of modified silica nanoparticles was made by adding 1 milliliter of SNOWTEX C®, available from Nissan Chemical Industries, Ltd., Houston, Tex., to 9 milliliters of deionized water. The suspension was pipetted in equal portions into four cuvets. Solutions of 0.01 percent by weight of each of copper chloride ($CuCl_2$), silver nitrate ($AgNO_3$), and zinc chloride ($ZnCl_2$), all from Aldrich Chemical Company, Milwaukee, Wis., were prepared and one drop of each was added to a separate cuvet. The Zeta Potential of each of the four suspensions was then measured by a Zetapals Unit, available from Brookhaven Instruments Corp., Holtsville, N.Y. The Zeta potential of the SNOWTEX C control suspension was measured to be −25 millivolts. The Zeta potential of both the SNOWTEX C/copper chloride suspension and the SNOWTEX C/silver nitrate suspension were measured to be −11 millivolts. The Zeta potential of the SNOWTEX C/zinc chloride suspension was measured to be −8 millivolts. The difference in Zeta Potential between the solutions was evidence that the metal ions had absorbed onto the silica nanoparticle.

Figure 2A:
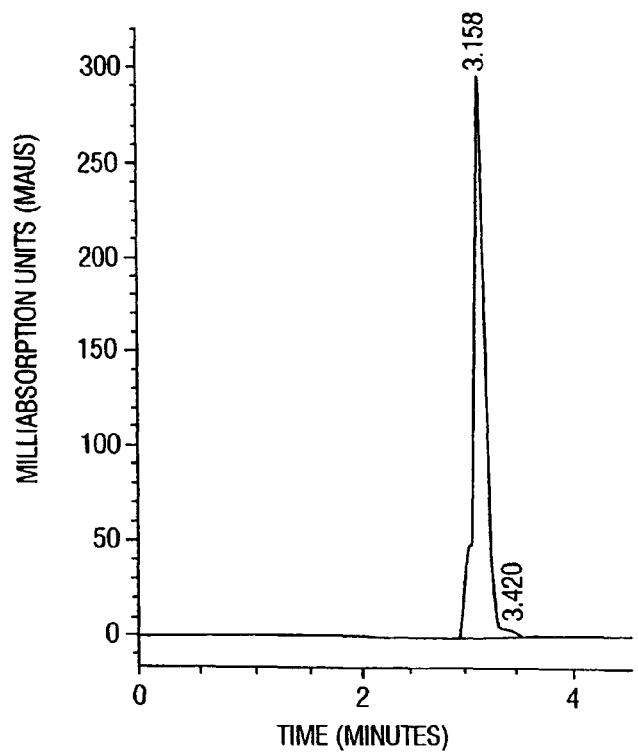
FIG. 2A is a high performance liquid chromatography chromatogram.

A furfuryl mercaptan solution was prepared for testing the odor removal properties of the modified silica nanoparticles. A stock solution of 0.001 percent by weight furfural mercaptan solution, available from Aldrich Chemical Co., Milwaukee, Wis., was made in distilled water. The solution had a strong odor. High performance liquid chromatography (HPLC) was used to measure concentration changes. A Zorbax Eclipse XDB-C18, 4.6 by 150 millimeter, 5 micron column was used along with 100 percent acetonitrile eluent. One microliter of the furfuryl mercaptan solution was injected into the HPLC column with a flow rate of 0.25 milliliters/minute. FIG. 2A, the generated HPLC chromatogram, shows furfuryl mercaptan peak to have an area of 16918 milliabsorption units·seconds (maus).

Figure 2B:
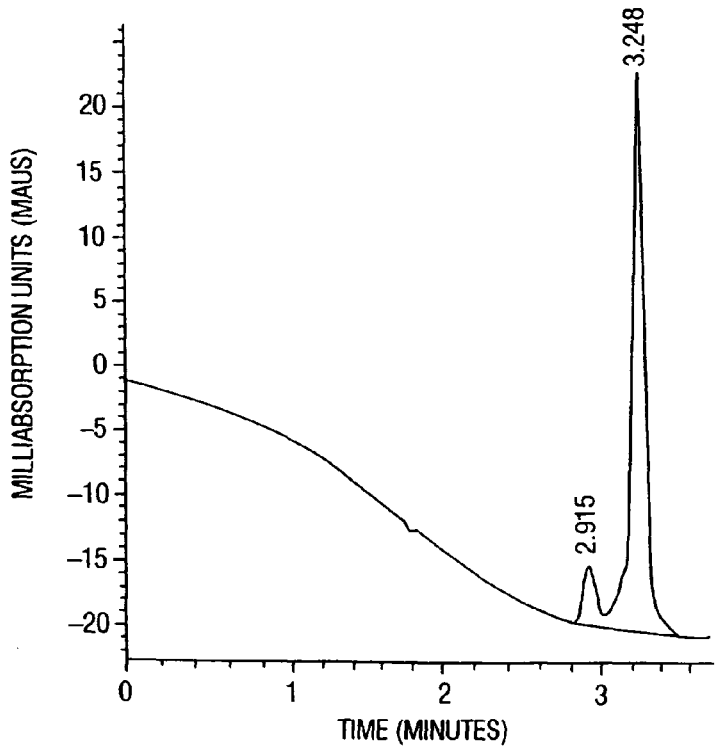
FIG. 2B is a high performance liquid chromatography chromatogram.

One drop of the SNOWTEX C/copper ion suspension was then added to 10 milliliters of the furfuryl mercaptan solution. The furfuryl mercaptan odor rapidly disappeared and one microliter of this furfuryl mercaptan solution was injected into the HPLC column with a flow rate of 0.25 milliliters/minute. FIG. 2B, the generated HPLC chromatogram, shows the furfuryl mercaptan peak to have an area of 188 milliabsorption units·seconds (maus). The concentration of the furfuryl mercaptan was greatly reduced, and the detectable odor as well, with the addition of the modified nanoparticles.

Example 2

Figure 3A:
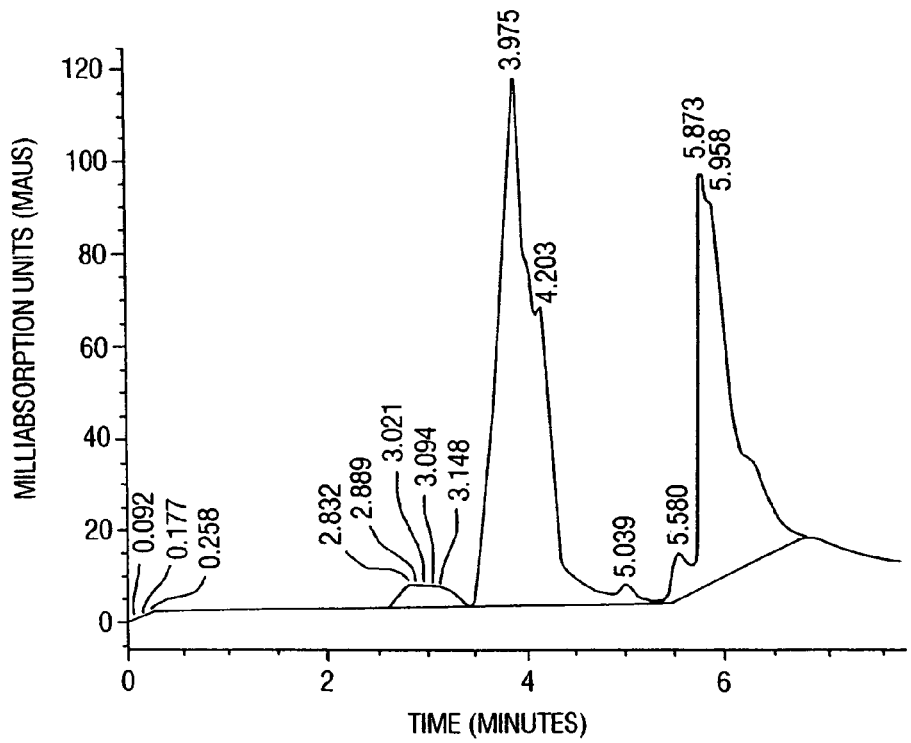
FIG. 3A is a high performance liquid chromatography chromatogram.
Figure 3B:
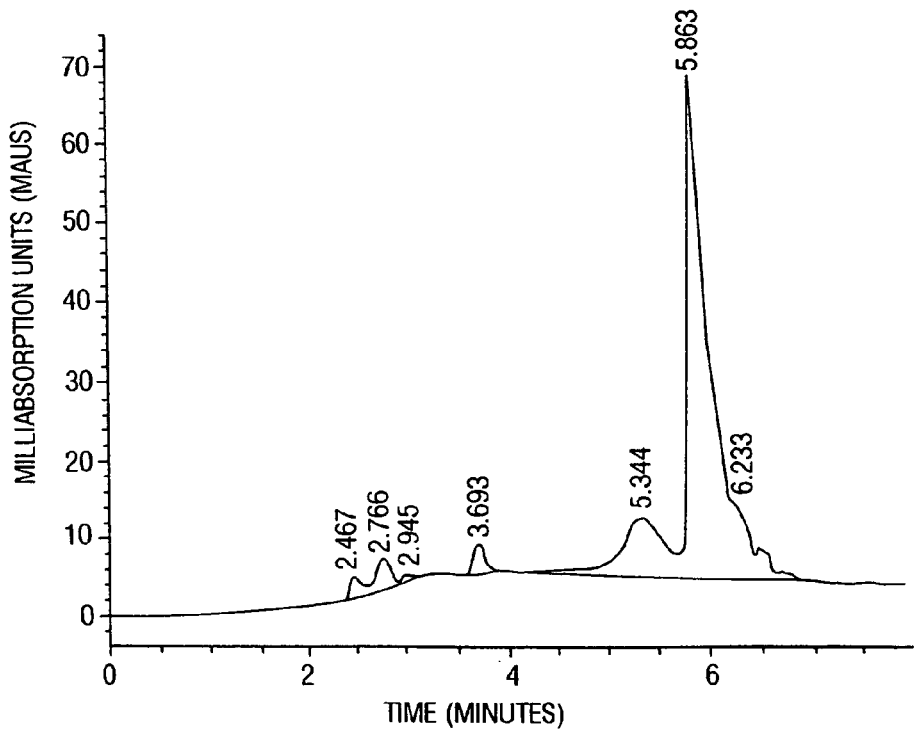
FIG. 3B is a high performance liquid chromatography chromatogram.

The SNOWTEX C/copper ion suspension was tested on human urine to determine the effectiveness in odor reduction. HPLC, as described in Example 1, was used to measure the components of urine (obtained from the inventor). One drop of the SNOWTEX C/copper ion suspension from Example 1 was tested against 0.1 gram of Purite Micronet MN-150 latex particles, available from Purolite Company, Philadelphia, Pa., and 0.1 gram of activated charcoal, available from Aldrich Chemical Co., Milwaukee, Wis. Each of these was added to a separate 3 grams of urine. The urine odor of the sample with the SNOWTEX C/copper ion suspension was almost completely eliminated after 3-5 seconds, compared to about 10 minutes for the activated charcoal. The latex particles never did remove the odor. FIG. 3A shows the HPLC chromatogram of the urine sample and FIG. 3B shows the chromatogram of the urine sample after the modified silica nanoparticles were added. Table 1 summarized the comparison of the HPLC peaks for the 4 samples. The modified silica nanoparticles performed substantially better in removing the urine components then the present commercial materials.

TABLE 1

| | Urine component HPLC peaks (peak retention time (minutes)) | | | | | |
| --- | --- | --- | --- | --- | --- | --- |
| Sample | area of peak at 3.87 min. | area of peak at 4.04 min. | area of peak at 4.77 min. | area of peak at 5.64 min. | area of peak at 5.88 min. | area of peak at 6.23 min. |
| Urine | 924 maus | 345 maus | 50 maus | 17 maus | 829 maus | 228 maus |
| Urine + Modified Silica Nanoparticles | 0 | 0 | 12 maus | 0 | 701 maus | 2 maus |
| Urine + Purite Latex Particles | 773 maus | 300 maus | 0 | 17 maus | 820 maus | 156 maus |
| Urine + Activated Charcoal | 900 maus | 0 | 50 maus | 17 maus | 820 maus | 10 maus |

Example 3

Silica nanoparticles were obtained under the commercial name Snowtex OXS (Nissan Chemicals, Houston, Tex.) as an aqueous suspension (10% wt/wt). The stock solution (50 ml) was diluted with a solution of aqueous sodium bicarbonate (350 ml, 0.05 M, Aldrich Chemical Company, St. Louis, Mo.) to generate a solution with a final pH of 8.7. An aqueous solution of copper(II) chloride (0.799 g in 100 ml, Aldrich Chemical Company, St. Louis, Mo.) was added to the Snowtex solution via an addition funnel with vigorous stirring. After stirring for several hours, the solvent was removed from the resulting light blue solution in vacuo, the isolated solid was washed with several portions of distilled water and allowed to air dry at room temperature. The pale blue solids were pulverized to obtain a fine powder which was characterized via analytical methods to further probe the fundamental relationship between the silica and the metal. The procedure described above can also be adapted to prepare functional particles with other metals, including iron or manganese, which can then also be evaluated using analytical methods to probe the relationship between silica particle and metal.

Example 4

Silica nanoparticles were obtained under the commercial name Snowtex OXS (Nissan Chemicals, Houston, Tex.) as an aqueous suspension (10% wt/wt). The stock solution (50 ml) was diluted with a solution of aqueous sodium bicarbonate (350 ml, 0.05 M, Aldrich Chemical Company, St. Louis, Mo.) to generate a solution with a final pH of 8.7. An aqueous solution of iron(III) chloride hexahydrate (0.799 g in 100 ml, Aldrich Chemical Company, St. Louis, Mo.) was added to the Snowtex solution via an addition funnel with vigorous stirring. After stirring for several hours, the solvent was removed from the resulting golden yellow solution in vacuo, the isolated solid was washed with several portions of distilled water and allowed to air dry at room temperature. The pale yellow solids were pulverized to obtain a fine powder which was characterized via analytical methods to further probe the fundamental relationship between the silica and the metal. The procedure described above can also be adapted to prepare functional particles with other metals, including copper or manganese, which can then also be evaluated using analytical methods to probe the relationship between silica particle and metal.

Example 5

Figure 5:
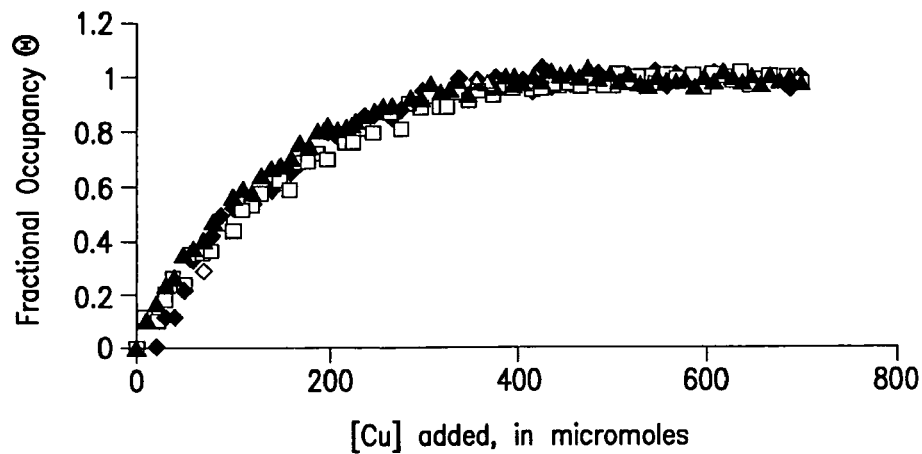
FIG. 5 is a Langmuir-isotherm plot generated using the data obtained for Example 5.

Titration experiments were carried out to probe the silica/metal ion relationship of the modified silica particles of Examples 3 and 4. The results suggested that the amount of metal present in the system correlated well with the molar ratio of metal salt added relative to the molar quantity of silica present, but that the quantity of metal that could coordinate did eventually plateau and was attributed to steric hindrance between metal ions. The number of metals coordinated to the particles was also dependent on the identity of the metal. Elemental analysis results confirmed the titration experiment findings. FIG. 5 is a Langmuir-isotherm plot generated using the data obtained from the titration experiments for the modified silica particles of Example 3 to show fractional occupation of the silica particle surface by the metal ion. The plot suggests a saturation point of approximately 56 copper ions per silica particle of Snowtex C.

Example 6

Figure 6:
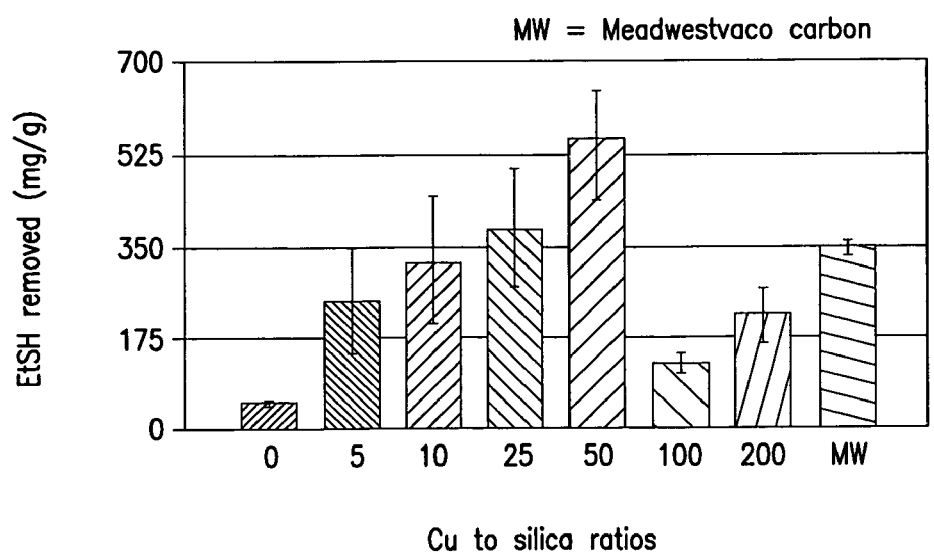
FIG. 6 is a bar graph summarizing data obtained for Example 6.

Gas chromatography was used to probe the effect of metal ion concentration and odor removal ability. Known quantities of the metal coated silica particle powders of Example 3 were placed in glass vials, model odorants were added to the vials (ethyl mercaptan, triethylamine, or isovaleraldehyde) and the contents were isolated by crimping a top onto the vial. These vials were then placed into a gas chromatograph equipped with a headspace analyzer and the ability of the powder to absorb the model odorants was evaluated against control samples containing no powder samples, only pure model odorant. The results suggest that moderate amounts of metal (i.e. 50-100 metal ions/silica particle) are more effective at odor removal than either smaller or larger quantities of metal. These results are attributed to decreased capacity and decreased availability of the metal ion to the odorant molecule due to increased steric hindrance, respectively. FIG. 6 is a bar graph showing data obtained for powder samples of copper modified silica particles at various copper ions to silica particle ratios (0 to 200) and their ability to remove ethyl mercaptan.

Example 7

After the analytical evaluation, the ability of the odor removal system was further assessed by creating treated substrates and generating more real world testing environments. The analytical evaluations described in both Examples 3 and 4 allowed for the solutions described in Example 3 to be used without further purification as the treating solutions for substrate preparation.

The following treatment solution was prepared:
Cu/OXS/PEI: 1 wt % silica in $NaHCO_3$ (aqueous), 50:1 Copper ion to silica particle ratio, 0.1 wt % PEI relative to silica weight; where "OXS" is SNOWTEX OXS silica nanoparticles in water suspension, available from Nissan Chemicals, Houston, Tex.; and "PEI" is poly(ethyleneimine) adhesive available under the trade name LUPASOL (Water-free, MW 25,000) from BASF Corporation. The PEI was added to increase the durability of the coating composition.

The following substrates were used in the following testing: 1) an IRONMAN airlaid cellulose and binder nonwoven web; 2) a polypropylene/polyethylene mix bonded carded web material (BCW); 3) a textured coform of cellulose and polypropylene laminate and a WYPALL hydroknit material; 4) a wire texture coform laminate (WTCL); all of which are available from Kimberly-Clark Corporation, Neenah, Wis.

Treated samples were made by a "dip-and-squeeze" technique utilizing an Atlas Laboratory Wringer type LW-1, available from Atlas Electric Devices Co., Chicago, Ill., equipped with a 5 lb. weight. Each sample was saturated with the corresponding treatment solution; then passed through the squeezing rollers. The samples were allowed to air dry, then double washed with de-ionized water and air dried again. The mass of each sample was recorded before treatment and after treatment, which was used for calculation of treatment add-on percentage.

A model odor generating composition was made for demonstrating the use and effectiveness of the modified high surface area material treated substrate of this invention to reduce refrigerator and garbage odors. A master batch of the odor composition was made with the following: 20 grams onions; 20 grams potato skins; 60 grams green cabbage; 40 grams Red Delicious apple peels; 40 grams orange peels; and 20 grams sardines (in water). Each of these materials was chopped into 2 cm×2 cm pieces, mixed by hand and placed into a plastic trash bag. The trash bag was sealed and stored at 20° C. for two days.

The efficacy of the treated material was compared with commercially available products. A key parameter in the selection of comparison products is the claim of odor removal or reduction, and not merely products generating fragrance or containing fragrance for masking odors. The following products were used as a comparison:

Control 1: ARM & HAMMER Fridge-N-Freezer Odor Absorber, 1 lb container designed for use in the refrigerator, available from Church & Dwight Company, Inc., Princeton, N.J.

Control 2: Natural Fridge odor absorber, 200 g gel designed for use in the refrigerator, available from IBA USA LLC, Santa Barbara, Calif.

For testing, an amount of the odor mixture was placed into an evaporation dish. Three 2.7 cubic feet compact refrigerators (Model no. HSP03WMAWW), available from Haier America, New York, N.Y., were used for the refrigeration tests. The refrigerators each included a fan for circulating air within the refrigerator.

Several studies were conducted using 4 to 6 volunteer panelists asked to assess the odor intensity of the individual refrigerators. The odor was assessed on regular intervals over a period of several hours. The odor ranking was rated 1 for the least odor up to the number of samples (e.g., 3 for refrigerator or 5 for garbage (below)) for the most odor. A simple arithmetical addition of the numbers produced the odor ranking. The results of these studies are provided in Tables 2-10.

For the refrigerator tests, the sheets were attached using double-sided foam SCOTCH mounting tape, available from 3M, to the left side of the top shelf on the inside of the refrigerator. When used in a test, the box of baking soda and the Natural Fridge odor absorber were placed on the left side of the top shelf.

Table 2 shows a comparison refrigerator test between a treated 4×6 sheets (about 10×15 cm) IRONMAN sheet, an untreated 4×6 sheets IRONMAN sheet, and the baking soda. An evaporation dish containing 200 g of the odor composition was placed into each of three refrigerators. At 7 hours, 20 hours, and 120 hours, the refrigerators were opened and the panelists were asked to rank the odors in each. As shown in Table 2, the modified silica nanoparticle treated sheet sticker provided a significant reduction of the odors inside the refrigerator. Of interest was the indication that baking soda does not reduce the odor as compared to the control.

TABLE 2

| Sample/Time | 7 hours (5 people rating) | 20 hours (6 people rating) | 120 hours (4 people rating) |
| --- | --- | --- | --- |
| Fridge 1 - Control | 13 | 15 | 9 |
| Fridge 2 - Baking Soda | 12 | 13 | 9 |
| Fridge 3 - Treated Sheet | 5 | 8 | 6 (least odor) |

To further demonstrate how effective the treated sheet was in absorbing refrigerator odors, the treated sheet sticker of Fridge 3 was transferred into the control Fridge 1 and the study continued. As shown in Table 3, after 23 hours the treated sheet reduced the odors in Fridge 1 to a ranking of the lowest malodor intensity level. Fridge 3, now without the treated sheet sticker, developed an intense malodor.

TABLE 3

| Sample/Time | 6 hours (5 people rating) | 23 hours (5 people rating) |
|---|---|---|
| Fridge 1 - Now with Treated Sheet | 10 | 6 (least odor) |
| Fridge 2 - Baking Soda | 11 | 12 |
| Fridge 3 - Now With Control Sheet | 9 | 12 |

The results in Table 3 clearly demonstrate the effectiveness of the treated nonwoven web sticker in absorbing malodor in the refrigerator. The treated nonwoven web sticker reduced the malodor significantly, such that Fridge 1 ranked lowest. Meanwhile, Fridge 3 (which previously contained the treated web) soon regained an odor intensity compared to baking soda after removing the treated web.

The odor assessments summarized in Table 4 were carried out to explore and identify the effect of substrate material on the odor reduction performance of the coating. 150 g of the odor composition was placed into each of three evaporation dishes. Each of the evaporation dishes was placed into one of the three refrigerators. A 4×6 inch sheet of each of the IRONMAN airlaid web and the BCW was treated, as described above, and placed, using the SCOTCH double-sided tape within a separate refrigerator. A 1 lb box of the baking soda was placed in the third refrigerator. At 28 hours the treated BCW was replaced with a treated WTCL and the study continued.

TABLE 4

| SAMPLE | 5 h (9 people) | 20 h (5 people) | 28 h | 48 h (5 people) | 56 h (6 people) |
|---|---|---|---|---|---|
| Treated IRONMAN Sheet | 14 | 5 | | 11 | 26 |
| Treated BCW Sheet | 40 | 28 | Replace with Treated WTCL | 20 | 16 |
| Baking Soda (1 lb box) | 38 | 43 | | 50 | 42 |

The treated IRONMAN and BCW sheets performed better than the baking soda box. Of the three types of sheets, the IRONMAN and the WTCL appeared to be more effective than BCW.

Fresh samples of the IRONMAN sheet and the WTCL sheet were prepared to confirm the results of Table 4. The test of Table 4 was repeated with the new samples and the results are summarized in Table 5.

TABLE 5

| SAMPLE | 6 h (5 people) | 20 h (4 people) | 44 h (3 people) | 68 h (3 people) |
|---|---|---|---|---|
| Treated WTCL Sheet | 22 | 15 | 16 | 10 |
| Treated IRONMAN Sheet | 13 | 13 | 3 | 3 |
| Baking Soda (1 lb box) | 36 | 37 | 30 | 30 |

The treated IRONMAN sheet shows significant odor reduction over the treated WTCL sheet. Baking soda generally performed poorly compared to all treated sheet stickers.

Table 6 summarizes the results of a comparison between the treated IRONMAN sheet and the Natural Fridge odor absorber. For the test of Table 6, 250 grams of the odor composition was placed into each of two evaporation dishes. Each of the evaporation dishes was placed into one of two refrigerators. A treated 4×6 inch IRONMAN sheet, as described above, was placed, using the SCOTCH double-sided tape, within one refrigerator. The Natural Fridge odor absorber was placed in another refrigerator.

TABLE 6

| SAMPLE | 87 h (4 people) | 16 h (4 people) | 40 h (4 people) |
|---|---|---|---|
| Natural Fridge | 24 | 24 | 19 |
| Treated IRONMAN Sheet | 19 | 14 | 4 |

The treated IRONMAN sheet demonstrated superior performance in significantly reducing the odor compared to the Natural Fridge odor absorber product.

Example 8

The following demonstrates the use and effectiveness of the treated substrate of this invention to reduce garbage odors. The garbage tests used 42 quart (40 liters) peddle trash cans, available from Sterilite Corporation, Townsend, Mass.

A 4×6 inch IRONMAN sheet was treated according to Example 7 above. The treated IRONMAN sheet and an untreated IRONMAN sheet were each attached to the underside of a trash can lid. An evaporation dish with 250 grams of the odor composition was placed into each of the two trash cans plus a third trash can without any sheet as a control. Table 7 summarizes the odor ranking by the panel at 3 hours and 7 hours.

TABLE 7

| SAMPLE | 3 h (6 people) | 7 h (5 people) |
|---|---|---|
| Control (untreated sheet) | 9 | 12 |
| Control (no sheet) | 14 | 9 |
| Treated IRONMAN Sheet | 13 | 7 (least odor) |

The treated sheet did not perform as well as in the refrigerator studies. This was likely due to the sheet not having an optimal placement within the trash can. As the odor components are generally heavier than air, the major concentration of the odor would be expected to reside toward the bottom of the trash cans.

Another study was carried out to examine the effect of sheet size and sheet placement on reducing odor. A larger 6×9 inch (about 15×23 cm) IRONMAN sheet and two smaller 4×6 inch IRONMAN sheets were all treated with the same Copper/OXS chemistry. Each of five trash cans was filled with 350 g of the odor generating composition in an evaporation dish. A small sachet (3 cm×3 cm) containing 1 g of copper ion modified silica particle (Cu/OXS) powder in a nonwoven fabric packet was also tried in this experiment. The powder samples of Cu/OXS (50:1 Copper ion to silica particle ratio)

were obtained as follows. For a 1 L total volume solution, a solution of $CuCl_2.2H_2O$ (0.9 g) in water (200 ml) was added to a solution of SNOWTEX OXS (92.5 ml SNOWTEX OXS plus 707.5 ml 0.05 M $NaHCO_3$ (aqueous)). The solution was stirred at ambient conditions for several hours, which was followed by removal of the solvent en vacuo. The pale blue precipitate was washed with several portions of de-ionized water and allowed to air dry.

Table 8 summarizes the results.

TABLE 8

| SAMPLE | 68 h (5 people) | 76 h (5 people) |
|---|---|---|
| Large IRONMAN Sheet - drop-in | 15 | 19 |
| Sachet drop-in | 15 | 12 |
| Control (no odor control agent) | 14 | 23 |
| Small IRONMAN Sheet - drop-in | 10 | 16 |
| Small IRONMAN Sheet -stick-up on lid | 6 (least odor) | 9 (least odor) |

The results in Table 8 show that the treated IRONMAN sheet stuck onto the trash can lid worked the best, exhibiting the lowest odor intensity across both time studies.

For the results in Table 9, 250 g of the odor composition (in an evaporation dish) was placed into each of five trash cans. One 4×6 inch BCW sheet, two 6×9 inch BCW sheets, and one 6×9 inch IRONMAN sheet were treated as in Example 3. The 4×6 inch BCW sheet was cut into a plurality of 0.5×0.5 cm pieces and sprinkled into one trash can containing the odor mixture. The other sheets were placed in the other trash cans as described in Table 9.

TABLE 9

| SAMPLE | 6 h (7 people) | 20 h (6 people) |
|---|---|---|
| Treated BCW Confetti | 11 | 11 |
| Control (no odor control agent) | 31 | 25 |
| Treated BCW Sheet (placed half-way down) | 26 | 14 |
| Treated IRONMAN Sheet (stuck on lid) | 15 | 14 |
| Treated BCW Sheet (stuck on lid) | 22 | 24 |

The IRONMAN sheet appeared to have superior odor absorbing properties compared to BCW sheet. However, by cutting the BCW into confetti, the performance improves, likely due to the enhanced surface area and proximity of the odor-absorbing material to the source of odor.

The above study was continued and extended to the WTCL substrate. 350 g of the odor composition (in an evaporation dish) was placed into each of four trash cans. One 4×6 inch WTCL sheet, two 6×9 inch BCW sheets, and two 4×6 inch IRONMAN sheets were treated as in Example 3. The sheets were placed in the other trash cans as described in Table 10.

TABLE 10

| SAMPLE | 16 h (5 people) | 24 h (6 people) |
|---|---|---|
| Control | 21 | 18 |
| Treated WTCL (on lid) | 16 | 15 |
| Treated IRONMAN Sheet (half-way down) | 16 | 14 |
| Treated IRONMAN Sheet (on lid) | 16 | 18 |

The IRONMAN sheet placed half-way down had the least odor followed closely by the WTCL sheet on the lid.

To compare the substrates when cut into confetti-like pieces, 250 g of the odor composition (in an evaporation dish) was placed into each of five trash cans. One WTCL sheet, one BCW sheet, and two IRONMAN sheets (all 4×6 inches) were treated as in Example 3, and all but one of the IRONMAN sheets were cut into 0.5 cm×0.5 cm confetti-like squares. The confetti-like pieces were sprinkled into the respective trash can over the odor composition. The IRONMAN airlaid web that was not cut into pieces was adhered with SCOTCH double-sided foam mounting tape to the inside lid of the fifth trash can. Four people were asked to rank the odor intensity of the five trash cans after 6 hours and 20 hours. Table 11 summarizes the rankings.

TABLE 11

| Sample/Time | 6 Hours | 20 Hours |
|---|---|---|
| Control (no treatment) | 10 | 13 |
| Treated WTCL Pieces | 8 | 11 |
| Treated BCW Pieces | 16 | 11 |
| Treated IRONMAN Pieces | 12 | 11 |
| Treated IRONMAN Sheet | 14 | 15 |

The odor reducing effectiveness of the modified silica nanoparticles does not appear to be influenced by the type of substrate material, e.g., thermoplastic material versus cellulose-based material (WTCL). However, the physical properties of the material, such as, for example, hydrophobicity versus hydrophilicity, may influence the odor removal ability in particular environments.

Example 9

The following demonstrates the use and effectiveness of the modified nanoparticles of this invention to reduce refrigerator odors when coated onto a free-standing container.

The copper coated silica particle solution was used to coat the exterior surface of an Arm and Hammer Fridge-N-Freezer Odor Absorber, 1 lb container available from Church & Dwight Company, Inc., Princeton, N.J. First, the sides of the box were abraded with a wire brush to remove the glossy coating. Next, the copper/Snowtex-OXS suspension of Example 7 was applied with a paint brush to wet the outside (approximately 0.1 g of modified nanoparticles as a dry coating added). The box was then allowed to dry at ambient temperature in a fume-hood. The refrigerator odor screening panel was used as described previously. In one refrigerator was placed the unopened box coated with the odor absorbing coating. The second refrigerator had an opened box of baking soda (control). Each refrigerator had 350 grams of the odor generating mixture and the refrigerators keep closed and the odor assessed after 12, 24, and 36 hours. Table 12 summarizes the results. The results clearly show the efficacy of the coating compared to one pound of baking soda

TABLE 12

Odor Assessment of Treated Box Versus Open Control Baking Soda.

| Sample | Odor Assessment 12 hour (4 panelists) | Odor Assessment 24 hour (4 panelists) | Odor Assessment 36 hour (4 panelists) |
|---|---|---|---|
| Control Box | 40 | 40 | 40 |
| Coated Box | 4 | 4 | 4 |

Initially, the waxy surface did not prove an ideal surface to coat, but after roughing up the surface to allow penetration into the more pulp-based portion of the substrate, the coating was readily absorbed. The testing environment and panel evaluation was as described in Example 7.

The panelists were in good agreement that the presence of the treated box within the refrigerator significantly reduced the amount of offensive odor present as compared to the control refrigerator, which contained a box in its original commercially available form. The results indicate that treating the surface of a three-dimensional container may also produce a functional odor removing object, increasing the variety of ways this odor control technology may be delivered.

Example 10

The odor removal properties of a modified nanoparticle when dry and coated on a surface was tested by coating a 10.16 centimeter square one-ply HI-COUNT® paper towel, available from Kimberly-Clark Corporation, Neenah, Wis., with the SNOWTEX C/copper ion suspension of Example 1 further diluted by 50 percent. The paper towel was coated by dipping the paper towel sample into the suspension. The wet paper towel was air-dried on a sheet of glass. The dried towel was placed over the mouth of a 100 milliliter beaker and held by a rubber band. The beaker contained 20 milliliter of the 0.001 percent by weight furfuryl mercaptan solution. A second untreated control HI-COUNT® paper towel was placed over an identical beaker as a control. The odors from the furfuryl mercaptans penetrated the untreated paper towel. However, no odors penetrated the paper towel treated with the modified nanoparticles for about three hours. After three hours the modified nanoparticles were saturated and the odors were detectable. The treated paper towel developed a dark area over the beaker during testing resulting from the binding of the furfuryl mercaptans.

Example 11

The odor removing properties of modified nanoparticles as an invisible coating on a bathroom tile was tested by treating a standard bathroom tile (15 centimeter×15 centimeter) from Home Depot with copper modified silica nanoparticles of Sample 1. The suspension of copper modified silica nanoparticles was applied to a KIM-WIPE®. The moist KIM-WIPE® was used to wipe the bathroom tile surface and a second dry KIM-WIPE® was used to wipe off any excess liquid. 3.6 microliters of ammonia, 28 percent ammonia in water, available from Aldrich Chemical Co., Milwaukee, Wis., was introduced to a laboratory desiccator via syringe and after 10 minutes an aliquot of the air/odor was sampled and analyzed to determine the concentration of ammonia in the desiccator. The experiment was repeated three times; once with no tile in the desiccator, once with an untreated control tile in the desiccator, and once with the modified nanoparticle treated tile in the desiccator. The ammonia gas was measured by use of a Drager tube, available from SKC, Inc., Pennsylvania, which could measure ammonia in air concentrations from 2 to 30 parts per million. A volume of 60 milliliters of the air/odor was pulled out of the desiccator by means of a syringe. The Drager tube was connected by Tygon tubing between the desiccator and the syringe. The ammonia concentration in the desiccator was measured at 20 parts per million with no tile and with the untreated tile. The ammonia concentration in the desiccator with the modified nanoparticle treated tile was measured at less than 2 parts per million. The modified nanoparticles on the standard bathroom tile were effective in substantially reducing ammonia gas and odor.

Example 12

The following further demonstrates the use and effectiveness of modified nanoparticles of this invention to reduce odors when coated onto a substrate and used as a wipe.

Garlic cloves were peeled, cut in half to expose the potent portion of the clove, and rubbed onto a bathroom tile to transfer the odor to it. Treated IRONMAN materials according to Example 7 were used to wipe off the garlic to see if they were capable of not only removing the odor from the tile, but capturing the odor as well. The tiles were wiped with the treated substrates using three strokes after the garlic was rubbed onto them, then the wipes and the tiles were each placed in separate sealed jars. Panelists were asked to evaluate the tile containing and wipe containing jars with respect to the presence of garlic odor after sitting at room temperature for 2-3 hours.

The panelists were in agreement that garlic odor was barely detectable in either tile containing jar (i.e., the one wiped with the untreated substrate or the one wiped with the treated substrates). This suggests that the garlic did not penetrate into the non-porous tile very rapidly. In contrast, the panelists noted a distinct difference in the presence of garlic odor in the wipe containing jars. The jar with the treated wipe was unanimously chosen as having the least amount of garlic odor as compared to the jar containing the untreated wipe. The treated wipe not only removed odors from the tile, but prevented the emanation of post-disposal odors.

Example 13

The following experiment demonstrates the use of modified nanoparticles of this invention in extending the shelf life of fruit. Permanganate modified alumina nanoparticles were adsorbed onto a 5.0 centimeter by 5.0 centimeter piece of 2 ounce spunbond polypropylene fabric at a level of 0.01 percent modified nanoparticle weight/fabric weight. The amount of permanganate ion was approximately 0.0001 percent ion weight/nanoparticle weight, monitored by measuring the change in nanoparticle Zeta Potential. Each of three yellow bananas with no brown spots from the same bunch was placed into an airtight bag. In the first airtight bag the modified nanoparticle treated fabric was placed. In the second bag contained an untreated 5.0 centimeter square spunbond polypropylene fabric as a control. The third bag contained no fabric piece also as a control. The three airtight bags were stored at ambient temperature for four weeks. At the end of four weeks the bananas in the two control bags were completely black, soft to the touch, and oozing liquid. The banana in the bag with the modified nanoparticle treated fabric was firm to the touch and had only a few brown markings. This demonstrated that the ripening process was slowed by the modified nanoparticles.

Example 14

To demonstrate the odor removing properties of modified organic nanoparticle of this invention copper ions were adsorbed onto polystyrene nanoparticles. A dilute suspension of modified polystyrene nanoparticles was made by adding 1.0 milliliter of polystyrene nanoparticle suspension, the nanoparticles having a particle diameter of 64 nanometers, available from Polysciences, Inc., Warrington, Pa., to 9.0 milliliters of deionized water. The polystyrene nanoparticle suspension had a Zeta Potential of −49 millivolts, as measured by the Zetapals Unit as in Example 1. Two drops of 0.01 percent by weight copper chloride ($CuCl_2$) solution was added to the polystyrene nanoparticle suspension. After the addition of the 2 drops of copper chloride solution the Zeta Potential of the polystyrene solution was measured at −16 millivolts, thus confirming copper ion adsorption onto the polystyrene nanoparticles. One drop of the modified nanoparticle solution was added to 2.0 milliliters of 0.001 percent by weight solution of furfuryl mercaptan. High performance liquid chromatography as described in Example 1 was used to measure furfuryl mercaptan presence before and after adding the modified nanoparticles. The area of the furfuryl mercaptan peak before the addition of the modified nanoparticles was 193 milliabsorption units, and after the addition of the modified nanoparticles it was 14 milliabsorption units. The copper modified polystyrene nanoparticles are useful in removing sulfurous compounds.

Example 15

A dilute suspension of modified silica nanoparticles was made by adding 1 milliliter of SNOWTEX C®, available from Nissan Chemical Industries, Ltd., Houston, Tex., to 9 milliliters of deionized water. The suspension was pipetted in equal portions into three different cuvets. Solutions of 0.01 percent by weight of each of copper chloride ($CuCl_2$), iron (II) chloride ($FeCl_2$), and iron (III) chloride ($FeCl_3$), all from Aldrich Chemical Company, Milwaukee, Wis., were prepared and one drop of each was added to a separate cuvet. The Zeta Potential of all three suspensions was then measured by a Zetapals Unit. The Zeta potential of the SNOWTEX C® control suspension was measured to be −22 millivolts. The Zeta potential of the SNOWTEX C/copper chloride suspension was measured at −10 millivolts, the SNOWTEX C/iron (II) chloride suspension at −13 millivolts, and the SNOWTEX C/iron (III) chloride suspension at +13 millivolts. One drop of each of the modified nanoparticle solutions was added to a separate 2.0 milliliter solution of 0.001 percent by weight furfuryl mercaptan. High performance liquid chromatography as described in Example 1 was used to measure furfuryl mercaptan presence before and after adding the different modified nanoparticles. The results are summarized in Table 12. Each of the modified nanoparticles were successful in removing furfural mercaptan from the solution. Additionally, iron (III) ion modified silica nanoparticles had a positive Zeta Potential which can allow application to fabrics made from materials such as polypropylene, polyethylene, nylon, and cotton, which have negative value streaming potentials.

TABLE 13

| Sample | Zeta Potential | Area of furfuryl mercaptan peak | Percent of odor removed |
| --- | --- | --- | --- |
| SNOWTEX C/$Cu^{+2}$ | −10 | 3.2 maus | 97% |
| SNOWTEX C/$Fe^{+2}$ | −13 | 38 maus | 67% |
| SNOWTEX C/$Fe^{+3}$ | +13 | 3.4 maus | 97% |

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

What is claimed is:

1. An odor absorbing article of manufacture, comprising:
a nonwoven web treated with a nanoparticle, the nanoparticle including silica, alumina, or combinations thereof and wherein the nanoparticle includes about 20-200 metal ions adsorbed onto the nanoparticle, wherein the adsorbed metal ions include copper ion, iron ion or combinations thereof and are active sites on a surface of the nanoparticle for binding gaseous or odorous compounds to the nanoparticle surface removing the compound from a surrounding environment.

2. The article of claim 1, wherein the odorous compound comprises a compound selected from the group consisting of sulfur containing compounds, nitrogen containing compounds, oxygen containing compounds, and combinations thereof.

3. The article of claim 1, wherein the substrate comprises a gas permeable material.

4. The article of claim 1, additionally comprising an adhesive material on one side of the substrate.

5. The article of claim 4, additionally comprising a removable layer disposed over the adhesive material on a side opposite the substrate.

6. The article of claim 1, further comprising a plurality of substrate pieces, the plurality of substrate pieces having an average piece outer surface area of about 1 $cm^2$ or less.

7. The article of claim 1, further comprising a plurality of substrate pieces, the plurality of substrate pieces having an average piece outer surface are of about 0.5 $cm^2$ or less.

8. The article of claim 1, wherein the nanoparticle comprises a surface area of at least about 200 square meters/gram.

9. The article of claim 1, wherein the article comprises a wipe.

10. An odor absorbing article of manufacture, comprising:
a nonwoven web; and
a plurality of modified nanoparticles on the nonwoven web, each of the plurality of modified nanoparticles including about 20-200 metal ions adsorbed per nanoparticle, the nanoparticle including silica, alumina, or combinations thereof, wherein each of the adsorbed metal ions is capable of binding at least one gaseous compound or odorous compound to the modified nanoparticle removing the compound from a surrounding environment.

11. The article of claim 10, wherein the plurality of metal ions comprises copper ions, iron ions, or combinations thereof.

12. The article of claim 10, additionally comprising an adhesive material on one side of the nonwoven web.

13. The article of claim 10, further comprising a plurality of nonwoven web pieces, the plurality of nonwoven web pieces having an average area of about 1 $cm^2$ or less.

14. An odor absorbing article of manufacture, comprising:
a nonwoven web; and
a plurality of modified silica nanoparticles on the nonwoven web, each of the plurality of modified silica nanoparticles including about 20-200 copper ions adsorbed per nanoparticle wherein each of the adsorbed copper ions is an active site on a surface of the silica nanoparticle for binding a gaseous or odorous compound to the silica nanoparticle surface removing the compound from a surrounding environment.

15. The article of claim 14, additionally comprising an adhesive material on one side of the nonwoven web.

16. The article of claim 14, further comprising a plurality of nonwoven web pieces, the plurality of nonwoven web pieces having an average piece outer surface area of about 1 cm² or less.

17. The article of claim 1, wherein the nanoparticle comprises a first Zeta Potential of about −1 to −50 millivolts and a second Zeta Potential after adsorption of the metal ions, the second Zeta Potential being higher than the first Zeta Potential as measured in a solution or suspension.

18. The article of claim 1, wherein the nanoparticle comprises a first Zeta Potential of about 1 to 70 millivolts and a second Zeta Potential after adsorption of the metal ions, the second Zeta Potential being lower than the first Zeta Potential as measured in a solution or suspension.

19. The article of claim 17, wherein the second Zeta Potential is at least about 5.0 millivolts higher than the first Zeta Potential as measured in a solution or suspension.

20. The article of claim 18, wherein the second Zeta Potential is at least about 5.0 millivolts lower than the first Zeta Potential as measured in a solution or suspension.

21. The article of claim 14, wherein the modified silica nanoparticles comprise a first Zeta Potential of about −1 to −50 millivolts and a second Zeta Potential after adsorption of the copper ions, the second Zeta Potential being higher than the first Zeta Potential as measured in a solution or suspension.

22. The article of claim 21, wherein the second Zeta Potential is at least about 5.0 millivolts higher than the first Zeta Potential as measured in a solution or suspension.

23. The article of claim 14, wherein the modified nanoparticles are coated on the nonwoven web in an amount of about 0.001 to 10.0 grams per square meter.

* * * * *